United States Patent
Kagaya et al.

(10) Patent No.: US 12,029,911 B2
(45) Date of Patent: Jul. 9, 2024

(54) MAGNETIC STIMULATION DEVICE

(71) Applicant: IFG CORPORATION, Miyagi (JP)

(72) Inventors: Hitoshi Kagaya, Aichi (JP); Shinichi Izumi, Miyagi (JP); Hitoshi Mori, Miyagi (JP); Kenji Yashima, Miyagi (JP)

(73) Assignee: IFG CORPORATION, Miyagi (JP)

(*) Notice: Subject to any disclaimer, the term of this patent is extended or adjusted under 35 U.S.C. 154(b) by 897 days.

(21) Appl. No.: 17/054,772

(22) PCT Filed: Jun. 28, 2018

(86) PCT No.: PCT/JP2018/024585
§ 371 (c)(1),
(2) Date: Nov. 11, 2020

(87) PCT Pub. No.: WO2020/003437
PCT Pub. Date: Jan. 2, 2020

(65) Prior Publication Data
US 2021/0244959 A1    Aug. 12, 2021

(51) Int. Cl.
*A61N 2/02*    (2006.01)
*A61N 2/00*    (2006.01)
(Continued)

(52) U.S. Cl.
CPC ............... *A61N 2/02* (2013.01); *A61N 2/006* (2013.01); *H01F 27/04* (2013.01); *H01F 27/2866* (2013.01)

(58) Field of Classification Search
CPC .......... A61N 2/02; A61N 2/006; H01F 27/04; H01F 27/2866; H01F 7/06
(Continued)

(56) References Cited

U.S. PATENT DOCUMENTS 5,480,373 A * 1/1996 Fischer ............... A61N 2/02
600/14
6,500,110 B1 * 12/2002 Davey ............... A61N 2/02
128/DIG. 25
(Continued)

FOREIGN PATENT DOCUMENTS

JP    S61-125006 U    8/1986
JP    H07-171220 A    7/1995
(Continued)

OTHER PUBLICATIONS

English Machine Translation of JP 2005237687 A, Sep. 8, 2005 (see attached) (Year: 2005).*
(Continued)

*Primary Examiner* — Sunita Reddy
(74) *Attorney, Agent, or Firm* — LUCAS & MERCANTI, LLP

(57) ABSTRACT

A magnetic stimulation device includes: a U-shaped magnetic core including a core body and a pair of legs extending in the same direction from the core body; conductors including a conductor having conductive layers that are wound around the leg and stacked in different levels and a conductor having conductive layers that are wound around the leg and stacked in different levels. The conductive layers and are each formed of a wire having a rectangular cross section that is parallel to the longitudinal direction of the legs, and are connected in parallel to the respective legs. Between the legs, the wires of the conductive layers around the leg are respectively connected, at each level, to the wires of the conductive layers around the second leg.

2 Claims, 11 Drawing Sheets

(51) Int. Cl.
  *H01F 27/04* (2006.01)
  *H01F 27/28* (2006.01)
(58) Field of Classification Search
  USPC ....................................................... 600/9–15
  See application file for complete search history.

(56) References Cited

U.S. PATENT DOCUMENTS

| | | | |
|---|---|---|---|
| 6,527,694 B1* | 3/2003 | Ishikawa | A61N 2/006 |
| | | | 600/9 |
| 2006/0287566 A1* | 12/2006 | Zangen | A61N 2/006 |
| | | | 600/15 |
| 2007/0027353 A1* | 2/2007 | Ghiron | A61N 2/006 |
| | | | 600/9 |
| 2011/0021863 A1* | 1/2011 | Burnett | A61N 2/006 |
| | | | 600/13 |
| 2012/0296150 A1* | 11/2012 | Pletnev | A61N 2/02 |
| | | | 600/13 |
| 2013/0317281 A1* | 11/2013 | Schneider | A61N 2/02 |
| | | | 600/13 |
| 2015/0080637 A1* | 3/2015 | Bonmassar | A61N 2/02 |
| | | | 600/14 |
| 2015/0099920 A1* | 4/2015 | Dobler | A61N 2/004 |
| | | | 600/14 |

FOREIGN PATENT DOCUMENTS

| | | |
|---|---|---|
| JP | H08-52231 A | 2/1996 |
| JP | H10-234870 A | 9/1998 |
| JP | 2000-504966 A | 4/2000 |
| JP | 2001-525947 A | 12/2001 |
| JP | 2002-306614 A | 10/2002 |
| JP | 2005-237687 A | 9/2005 |
| JP | 2009-226037 A | 10/2009 |
| JP | 2010-166971 A | 8/2010 |
| JP | 2014-188014 A | 10/2014 |
| JP | 2016-028640 A | 3/2016 |
| JP | 2017-184979 A | 10/2017 |
| WO | 98/06342 A1 | 2/1998 |
| WO | 2016/013146 A1 | 1/2016 |

OTHER PUBLICATIONS

EPO, European Search Report for the corresponding European Patent Application No. 18924324.9, dated Feb. 26, 2021.
PCT, International Search Report for the corresponding patent application No. PCT/JP2018/024585, dated Sep. 25, 2018, with English translation.
Chinese Patent Office, "Rejection Decision" dated Feb. 24, 2024, which was issued for the corresponding Chinese Patent Application No. 201880094270.X, with English translation, 15 pages.
Shinichi Izumi, "Magnetic Stimulation—Basic Principles and Applications" (in Japanese), Dec. 1, 2005, Ishiyaku Publishers, Inc., pp. 198-205, with English translation.
Shinichi Izumi, "Body and brain to recover Brain rehabilitation to treat stroke paralysis" (in Japanese), Sep. 20, 2009, Chuohoki Publishing Co., Ltd., pp. 183-196, with English translation.

* cited by examiner

[FIG. 1]
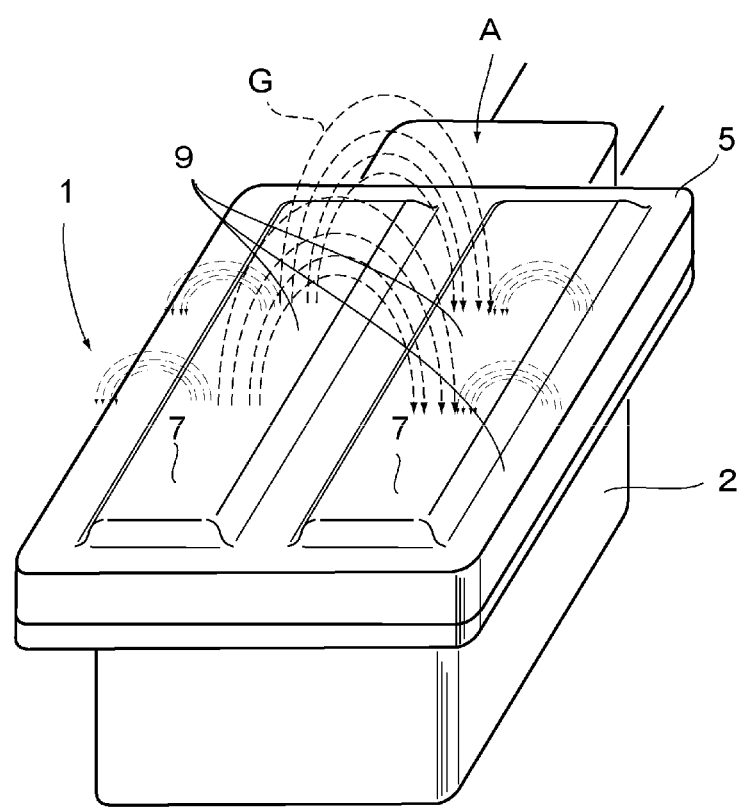

[FIG. 2]
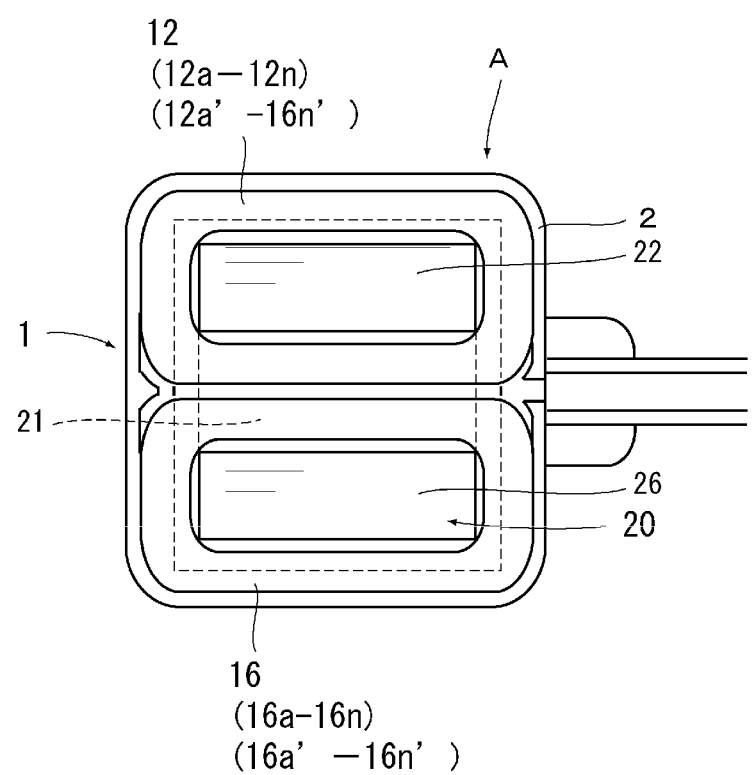

[FIG. 3]
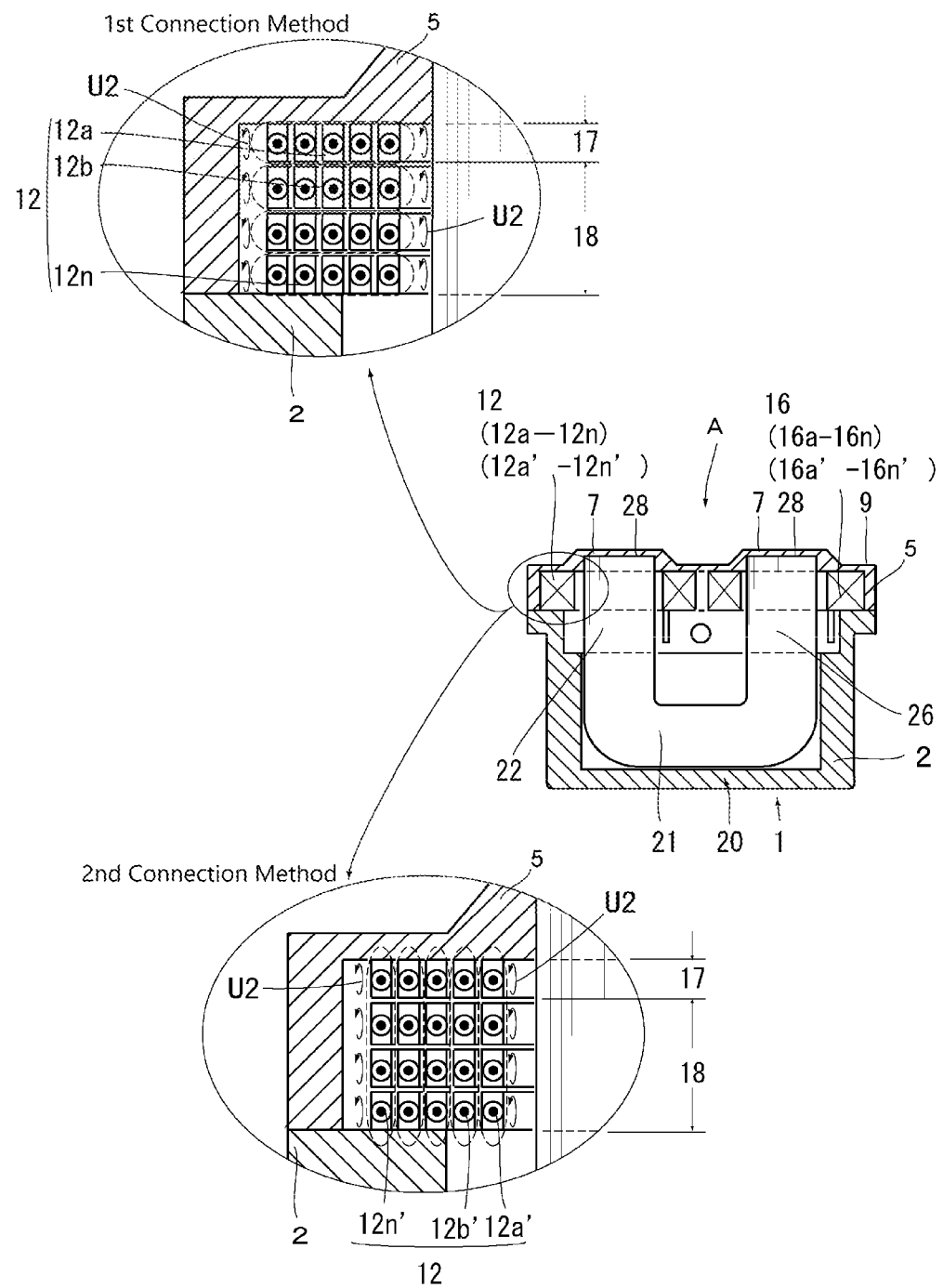

[FIG. 4]
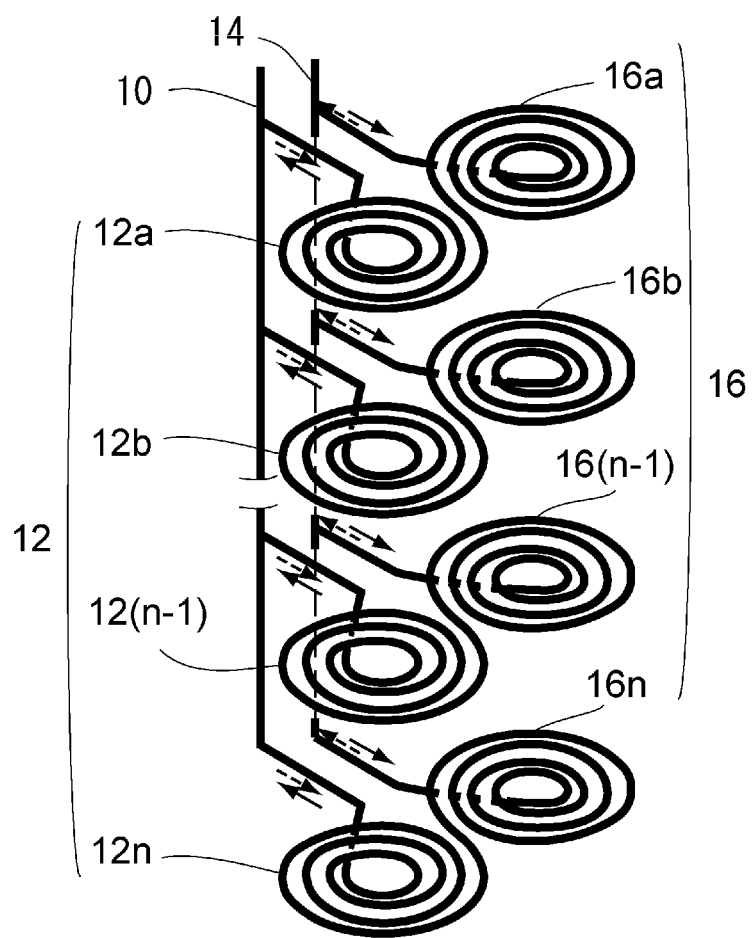

[FIG. 5]
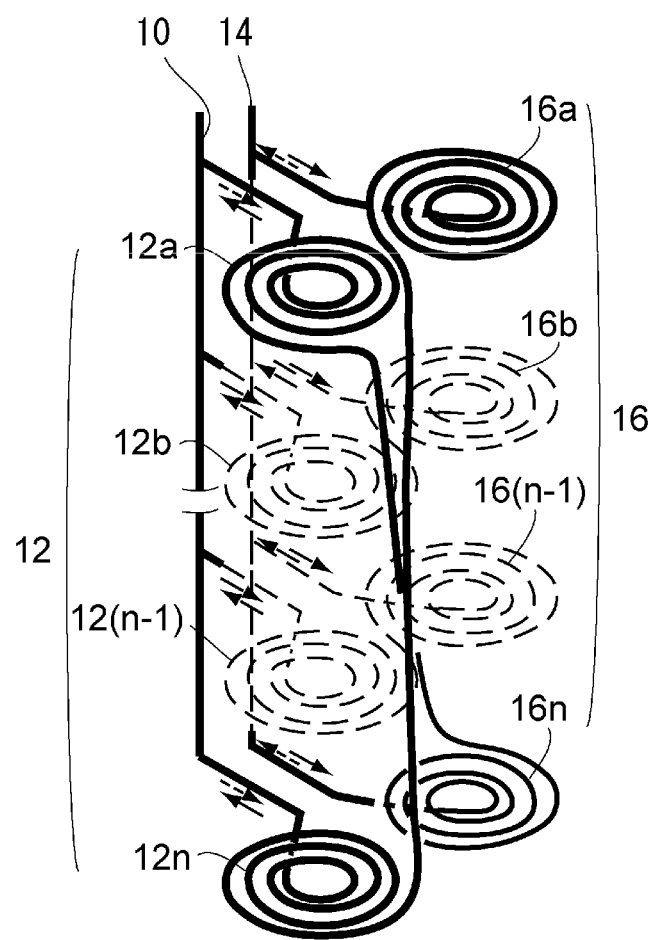

[FIG. 6]
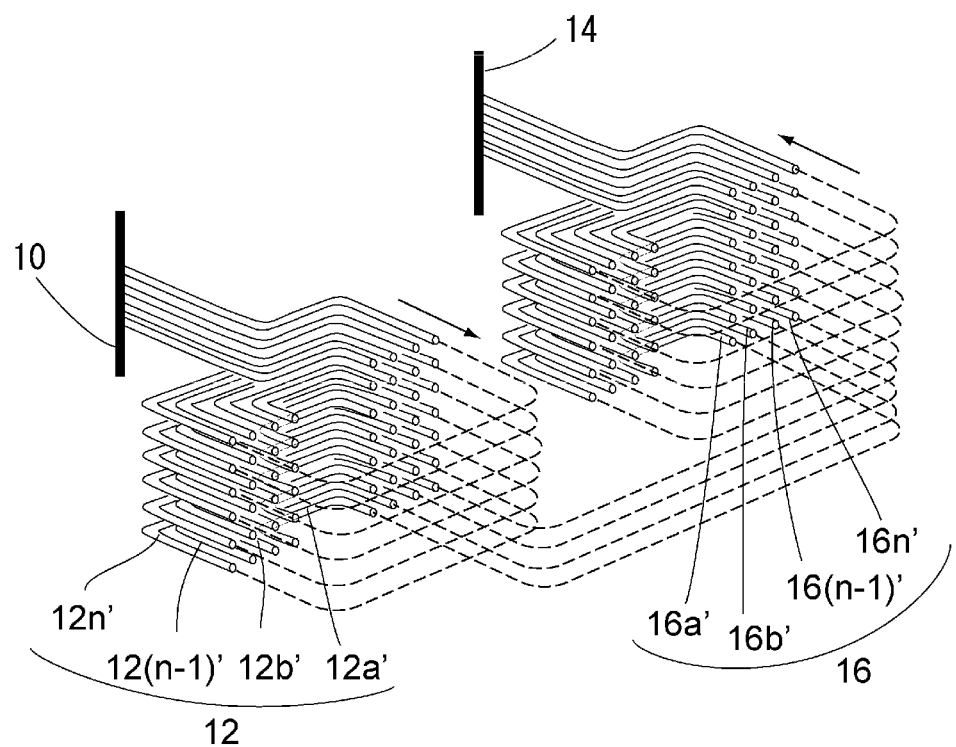

[FIG. 7]
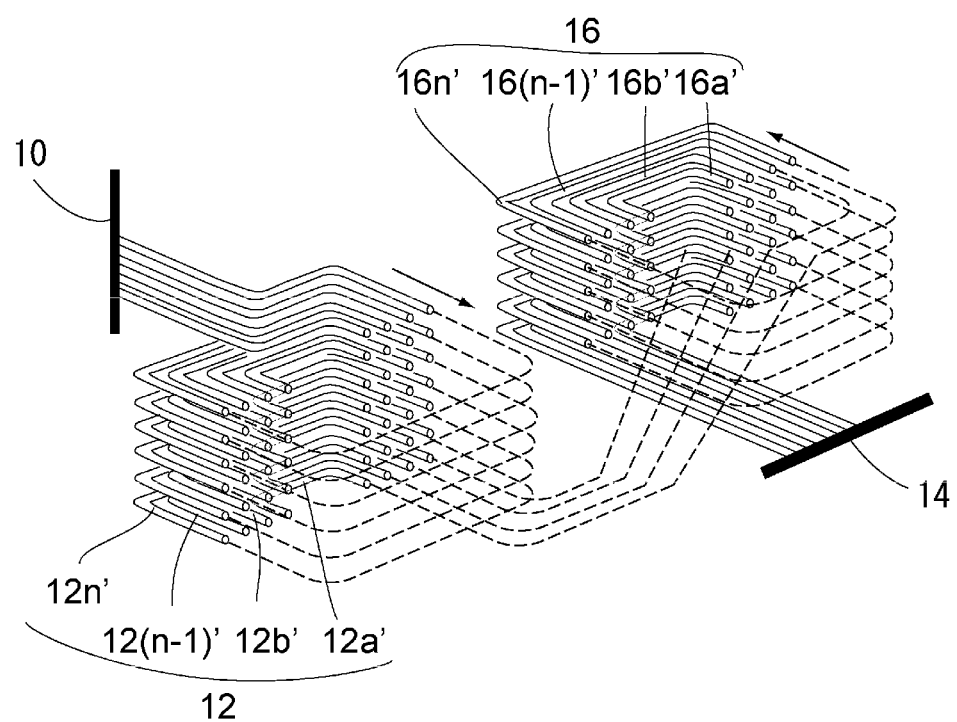

[FIG. 8]
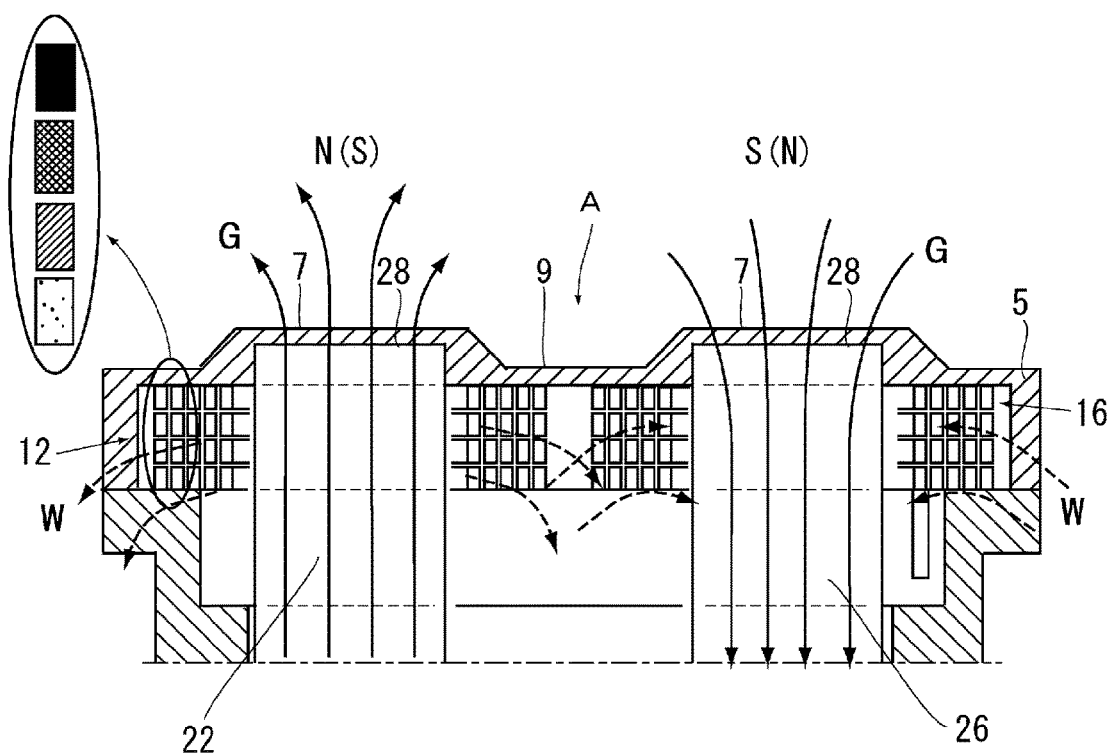

[FIG. 9]
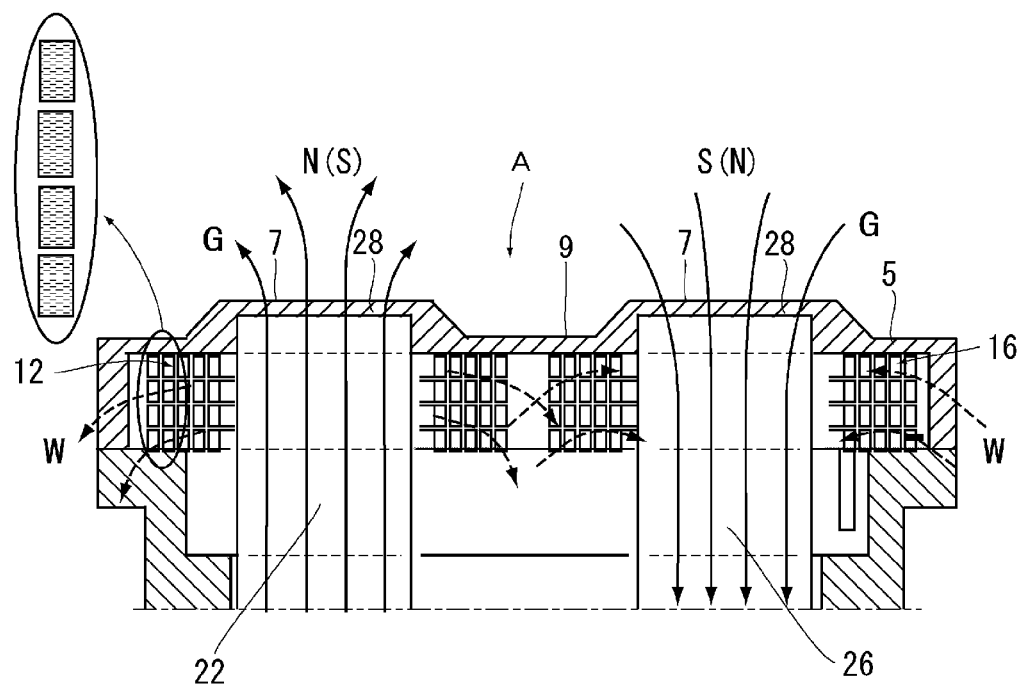

[FIG. 10]
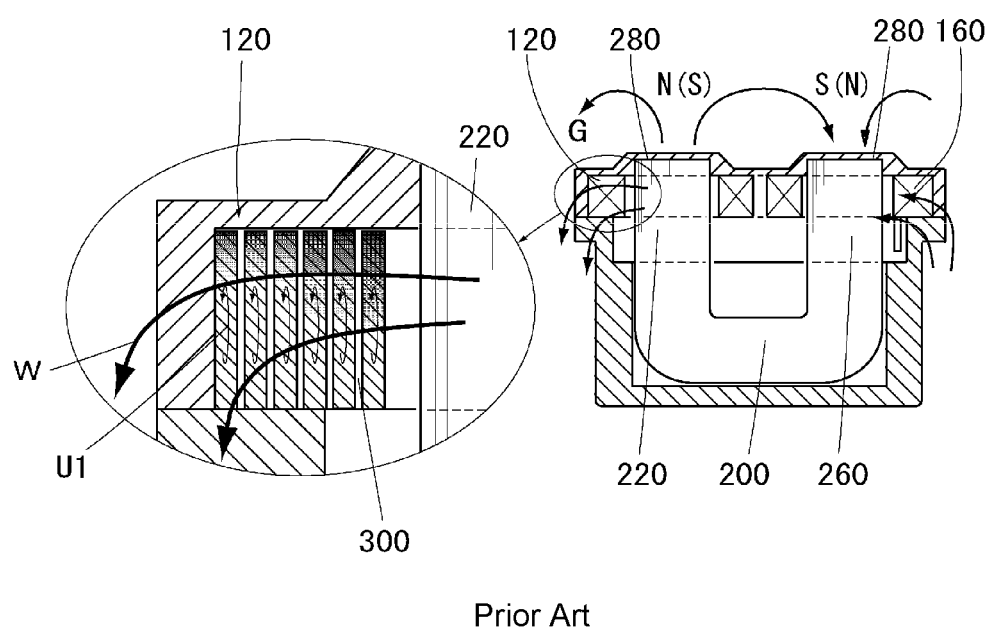
Prior Art

[FIG. 11]
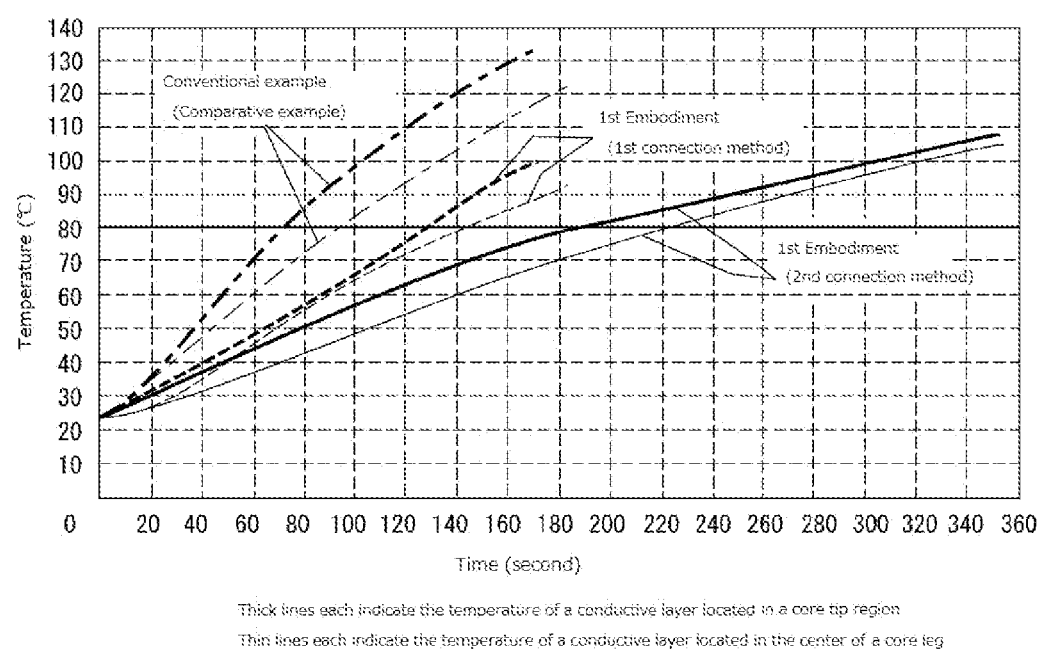

MAGNETIC STIMULATION DEVICE

CROSS REFERENCE TO RELATED APPLICATION

This Application is a 371 of PCT/JP2018/024585 filed on Jun. 28, 2018, the above application is incorporated herein by reference.

TECHNICAL FIELD

The present invention relates to a device for repeatedly applying magnetic stimulation to peripheral nerves or cerebral motor cortices using a coil having a magnetic core and a cooling mechanism so as to enhance the effect of the magnetic stimulation.

BACKGROUND ART

More than two million people are now suffering from paralysis of their limbs caused by sequelae of cerebrovascular disorders and spinal cord injuries, and the number of such paralytic patients is still increasing due to a change in the age structure of the Japanese population. Since paralysis persisting for a long period of time can cause a significant decrease in muscle function as a result of disuse syndrome, it is difficult for the patient to recover from the paralysis. Rehabilitation as a type of exercise therapy is considered to be the most important treatment to prevent disuse syndrome caused by hemiplegia or quadriplegia and to promote recovery of muscle function.

Due to a change in the age structure of the Japanese population, dysphagia (difficulty in swallowing) as sequelae of cerebrovascular disorders or caused by aging is also becoming a social problem. The majority of pneumonia cases (pneumonia is the third leading cause of death in Japan) are aspiration pneumonia cases caused by dysphagia. As a means of rehabilitation for dysphagia, exercise therapy such as repetitive activation of swallowing-related muscles is often used.

On the other hand, as another type of rehabilitation without exercise therapy, a technique for electrically stimulating peripheral nerves or cerebral motor cortices to induce movement of muscles is known. As an electrical stimulation technique, transcutaneous electrical nerve stimulation (TENS) is widely used. This technique is based on the principle of electrically stimulating motor nerves externally to induce contraction of limb muscles and thereby recover motor function. Likewise, as a device for rehabilitation of dysphagia, a medical device for electrically stimulating submandibular muscles to induce contraction of swallowing-related muscles has been recently developed. Strong electrical stimulation is required to allow the stimulation to induce a significant contraction of muscles. Like an electric shock, such strong electrical stimulation causes acute discomfort or pain. Various studies, such as improvements in frequency and waveform, have been conducted to relieve this discomfort or pain, but no satisfactory solution has been found.

Pain caused by electrical stimulation is detected by pain receptors distributed just below the skin. Therefore, such pain caused by electrical stimulation can be relieved by embedding stimulation electrodes under the skin. However, signal lines from the embedded electrodes must always be located outside the body, which poses a potential risk of bacterial infection of the wounds.

A technique for electromagnetically stimulating nerves without using a contact electrode is magnetic stimulation. In this technique, when a pulse current is supplied to a coil placed near the surface of a body to cause the coil to generate a magnetic flux, the magnetic flux thus generated causes an electric current to be induced in the body, and the induced current stimulates the nerves to activate the muscles. This magnetic stimulation technique does not require a step of attaching or embedding electrodes and, in addition, this technique causes little pain or discomfort, unlike an electric shock.

For these reasons, magnetic stimulation has advantages, such as stronger stimulation and greater muscle contraction, over the above-mentioned electrical stimulation. Therefore, magnetic stimulation has been widely applied to diagnosis and treatment of diseases and practically used as transcranial magnetic stimulation (TMS). In particular, a combination of TMS, in which magnetic stimulation is repeated, and exercise therapy enhances the effect of rehabilitation (see Non-Patent Literatures 1 and 2).

An invention of using muscle contraction induced by magnetic stimulation is a urinary incontinence treatment device of Patent Literature 1. This device includes a magnetic stimulation coil, and is configured to allow the coil, when fixed to a chair or attached to a body, to generate a pulsed magnetic field of 0.01 to 3 Tesla at 1 to 100 Hz so as to repeat periodic contraction of bladder sphincter for urinary incontinence treatment.

Unlike the technique of merely inducing contraction of muscles for urinary incontinence treatment, a technique disclosed in Patent Literature 2 is to bend a finger or an arm repeatedly by magnetic stimulation. Patent Literature 2 indicates that when magnetic pulses are applied at intervals of 10 milliseconds to stimulate the nerves of the arm, the arm's bending distance increases as the number of pulses increases.

The effect of magnetic stimulation increases as the number of repetitions of magnetic stimulation increases. However, a high current of more than several hundred amperes must flow through a coil to cause magnetic stimulation to occur. Thus, magnetic stimulation using successive pulses has a drawback that significant heat generation and temperature rise occur in the coil and thus the number of pulses cannot be increased. This heat generation is a serious technical constraint on successive magnetic stimulation.

In order to reduce heat generation in a magnetic stimulation coil, it is effective to use a coil with a magnetic core capable of generating a strong magnetic field with a low electric current. Therefore, patent applications for a magnetic stimulation coil with a magnetic core for transcranial magnetic stimulation have been filed. Patent Literature 3 discloses a magnetic stimulation device including: a magnetic core obtained by cutting a portion of an O-shaped (toroidal) magnetic core to form opposite end portions and tapering the end portions: and coils each wound around the tapered end portions so as to generate a converging magnetic field.

Patent Literature 4 discloses, as an improvement of the above-mentioned device of Patent Literature 2, a magnetic stimulation device including a winding and a magnetic material disposed in a space formed within the winding. Furthermore, Patent Literature 5 describes a technique of transcranial magnetic stimulation, in which a coil is wound around a semicircular or horseshoe-shaped magnetic core having a high magnetic permeability to apply magnetic stimulation to brains while reducing heat generation in the coil. Patent Literature 6 discloses a technique of using a ferromagnetic material having a high magnetic permeability and saturation magnetic flux density for a magnetic core having a shape similar to that of Patent Literature 5.

Patent Literature 7 describes a technique of using a coil with strands of thin litz wires wound thereon, as a well-known example of high frequency coils, and thereby reducing heat generation in the coil. However, in a litz wire coil, the ratio of the cross-sectional area of the insulating portion (including the gap between the windings of the coil) to that of the conducting portion is high and therefore the electrical resistance is high for the cross-sectional area of the litz wire itself. In addition, since the litz wires insulated with a less thermally conductive material are wound several times, the coils are thermally insulated with several layers of the insulating material and therefore the heat in the inner layers hardly escapes to the outside. For these reasons, the temperature of the coil rises to an allowable temperature limit or higher.

While this technique has these heat-related problems, it has the advantage that it has a strong magnetic stimulation effect through successive magnetic stimulation and thereby can induce significant movement of muscles of fingers and limbs.

Under these circumstances, assuming that heat generation in a coil cannot be avoided, the inventors have developed a method as disclosed in Patent Literature 8.

CITATION LIST

Non-Patent Literature

[NPTL 1] S. Izumi: Jikishigeki-ho no Kiso to Oyo. Noukekkan Shogai (in Japanese), Ishiyaku Publishers, Inc., page 198

[NPTL 2] S. Izumi: Kaifuku-suru Shintai to Nou. Jikishigeki-niyori Mahiga Kaizen-shita Rei (in Japanese), Chuohoki Publishing Co., Ltd., page 183

Patent Literature

[PTL 1] Japanese Unexamined Patent Application Publication No. 10-234870

[PTL 2] Japanese Unexamined Patent Application Publication No. 2010-166971

[PTL 3] Japanese Unexamined Patent Application Publication No. 7-171220

[PTL 4] Japanese Unexamined Patent Application Publication No. 8-52231

[PTL 5] Japanese Translation of PCT International Application Publication No. JP-T-2000-504966

[PTL 6] Japanese Translation of PCT International Application Publication No. JP-T-2001-525947

[PTL 7] Japanese Unexamined Patent Application Publication No. 2002-306614

[PTL 8] Japanese Unexamined Patent Application Publication No. 2016-28640

SUMMARY OF INVENTION

Technical Problem

The means disclosed in Patent Literature 8 is configured to cool a magnetic core, a conductor itself serving as a coil, and a gap between the magnetic core and a skin contact surface of a casing so as to suppress a temperature rise of the skin contact surface of the casing. The device is schematically configured as shown in FIG. 10. Conductors 120 and 160, which are each made of a wide strip with a rectangular cross section (for example, a copper strip with a cross section of 0.8 mm×9 mm), are respectively wound around legs 220 and 260 of a U-shaped core 200 with the rectangular cross section being in portrait orientation (i.e., with the longitudinal direction of the rectangular cross section of the copper strip extending along the longitudinal direction of the legs 220 and 260). At the time of the invention, it is unknown why heat is generated in the conductors 120 and 160 when a current is supplied to them. Therefore, the cooling gaps 300 are provided as a means of cooling the conductors 120 and 160 and the legs 220 and 260 of the U-shaped core 200, thereby solving the problem of temperature rise.

However, this method has the following problems: the cooling gaps must be provided between the layers of the conductors 120 and 160, in other words, the size of the device is increased by the size of the cooling gaps: the area efficiency of the entire conductors 120 and 160 (i.e., the ratio of the area of the electrically conductive portions to the cross-sectional area of the entire conductors) decreases: a cooling mechanism for supplying a cooling gas to the casing (for example, a cooling fan or a cooling gas supply tube) is needed, and thus, for example, the weight of the device is increased by the weight of the cooling fan, or the presence of the tube makes the device harder to use.

The present invention has been made in view of these conventional technical problems, and it is an object of the present invention to provide a magnetic stimulation device with an ingenious conductor structure, capable of reducing heat generation in the conductor itself and thereby suppressing an increase in the temperature of a skin contact surface of the device.

Solution to Problem

Claim 1 relates to a first structure (multi-level spiral structure: First embodiment) of conductors 12 and 16 of a magnetic stimulation device A of the present invention (FIG. 1 to FIG. 5).

The magnetic stimulation device A includes: a magnetic core 20 including: a core body 21: and a pair of first and second legs 22 and 26 extending from the core body 21: and conductors including: a conductor 12 having conductive layers 12a-12n that are wound around the first leg 22 and stacked in different levels: and a conductor 16 having conductive layers 16a-16n that are wound around the second leg 26 and stacked in different levels.

In the magnetic stimulation device A, the conductive layers 12a-12n and 16a-16n are each formed of a wire having a rectangular cross section that is parallel to a longitudinal direction of the first and second legs 22 and 26, and between the pair of first and second legs 22 and 26, the wires of the conductive layers 12a-12n around the first leg 22 are respectively connected, at each level, to the wires of the conductive layers 16a-16n around the second leg 26.

Claim 2 relates to a first connection method (FIG. 4) for the magnetic stimulation device A according to claim 1.

In the magnetic stimulation device A, a leg tip 28-side first layer 12a of the conductive layers 12a-12n wound around the first leg 22 in different levels is connected to a leg tip 28-side first layer 16a of the conductive layers 16a-16n wound around the second leg 26 in different levels, and second to nth layers around the first leg 22 are respectively connected in this order to second to nth layers around the second leg 26 at the same level.

Claim 3 relates to a second connection method (FIG. 5) for the magnetic stimulation device A according to claim 1.

In the magnetic stimulation device A, a leg tip 28-side first layer 12a of the conductive layers 12a-12n wound around the first leg 22 in different levels is connected to a core body 21-side nth layer 16n of the conductive layers 16a-16n wound around the second leg 26 in different levels, a core body 21-side nth layer 12n around the first leg 22 is connected to a leg tip 28-side first layer 16a of the conductive layers 16a-16n wound around the second leg 26 in different levels, and second to (n−1)th layers 12b-12(n−1) around the first leg 22 are respectively connected in reverse order to (n−1) th to second layers 16(n−1)-16b around the second leg 26.

Claim 4 relates to a second structure (concentric multilayer coil spring-like structure: Second embodiment) of the conductors 12 and 16 of the magnetic stimulation device A of the present invention (FIG. 1 to FIG. 3, FIG. 6, and FIG. 7).

The magnetic stimulation device A includes: a magnetic core 20 including: a core body 21; and a pair of first and second legs 22 and 26 extending from the core body 21; and conductors including: a conductor 12 having conductive layers 12a'-12n' that are wound around the first leg 22 in concentric layers of different diameters or dimensions; and a conductor 16 having conductive layers 16a'-16n' that are wound around the second leg 26 in concentric layers of different diameters or dimensions.

In the magnetic stimulation device A, the conductors 12 and 16 are each formed of wires having a rectangular cross section that is parallel to a longitudinal direction of the first and second legs 22 and 26, and between the pair of first and second legs 22 and 26, the wires of the conductive layers 12a'-12n' around the first leg 22 are respectively connected, at each concentric position, to the wires of the conductive layers 16a'-16n' around the second leg 26.

Claim 5 relates to a first connection method (FIG. 6) for the magnetic stimulation device A according to claim 4.

In the magnetic stimulation device A, a leg 22-side innermost first layer 12a' of the conductive layers 12a'-12n' wound around the first leg 22 in concentric layers is connected to a leg 26-side innermost first layer 16a' of the conductive layers 16a'-16n' wound around the second leg 26 in concentric layers, and second to nth layers 12b'-12n' around the first leg 22 are respectively connected in this order to second to nth layers 16b'-16n' around the second leg 26 at the same concentric position.

Claim 6 relates to a second connection method (FIG. 7) for the magnetic stimulation device A according to claim 4.

In the magnetic stimulation device A, a leg 22-side innermost first layer 12a of the conductive layers 12a-12n' wound around the first leg 22 in concentric layers is connected to an outermost nth layer 16n' of the conductive layers 16a-16n' wound around the second leg 26 in concentric layers, an outermost nth layer 12n' around the first leg 22 is connected to a leg 26-side innermost first layer 16a' of the conductive layers 16a'-16n' wound around the second leg 26 in concentric layers, and second to (n−1)th layers 12b'-12(n−1)' around the first leg 22 are respectively connected in reverse order to (n−1) th to second layers 16(n−1)'-16b' around the second leg 26.

Advantageous Effects of the Invention

According to the magnetic stimulation device A of the present invention configured as described above, the amount of heat generated in the conductors 12 and 16 is reduced for the following reasons. As a result, when a treatment is applied using this device, it is possible to maintain the temperature of the affected area contact surface 9 of the casing 1 containing the magnetic core 20 within a safe temperature range for a period of time necessary for the treatment (for example, at least 2 to 3 minutes). Therefore, the device does not cause thermal damage such as burns in the affected area.

This magnetic stimulation device A makes it possible to use the effect of a pulsed magnetic field so as to successively and greatly move muscles that cannot voluntarily move due to paralysis caused by brain dysfunction, etc. The same muscle contraction effect can also be obtained by electrical stimulation. However, electrical stimulation has the following drawbacks: (1) it causes pain or discomfort like electric shock: (2) it takes time and trouble to attach or embed electrodes: and (3) it may cause burns when a current is supplied. However, magnetic stimulation is free from these drawbacks (1) to (3). Even if quadriplegia occurs due to brain dysfunction, nervous system and muscles are not damaged. Therefore, appropriate rehabilitation treatment can recover motor function. However, prolonged impaired consciousness or bedridden state may cause disuse syndrome, thereby hindering recovery of motor function. When successive magnetic stimulation is applied using the magnetic stimulation device A of the present invention, paralyzed muscles of limbs and fingers can be moved effectively. Therefore, it can be expected that rehabilitation effect can be dramatically enhanced.

BRIEF DESCRIPTION OF DRAWINGS

FIG. 1 is a perspective view of a magnetic stimulation device of the present invention.

FIG. 2 is a plan view of FIG. 1, from which a lid is removed.

FIG. 3 shows cross-sectional views of FIG. 1.

FIG. 4 is a perspective view of a main part of the device, showing a first connection method in a first conductor structure of FIG. 3.

FIG. 5 is a perspective view of a main part of the device, showing a second connection method in the first conductor structure of FIG. 3.

FIG. 6 is a perspective view of a main part of the device, showing a first connection method in a second conductor structure.

FIG. 7 is a perspective view of a main part of the device, showing a second connection method in the second conductor structure.

FIG. 8 is a cross-sectional view of the device, showing heat generation distribution in the conductors shown in FIG. 4 when a current is supplied to them.

FIG. 9 is a cross-sectional view of the device, showing heat generation distribution in the conductors shown in FIG. 5 to FIG. 7 when a current is supplied to them.

FIG. 10 is a cross-sectional view of a conventional example in which magnetic flux leakage occurs.

FIG. 11 is a graph showing a comparison between heat generation in a conventional example and that in the present invention.

DESCRIPTION OF EMBODIMENTS

Next, the present invention will be described in detail by way of embodiments. These embodiments are given for easy understanding by those skilled in the art. That is, it is to be understood that the present invention should not be limited only by these embodiments but should be limited only by the technical idea described in the entire specification of the present invention.

The main components of the magnetic stimulation device A of the present invention are conductors 12 and 16 and a magnetic core 20, which are housed in a casing 1.

The magnetic core 20 is a U-shaped member including a core body 21 and a pair of legs 22 and 26 extending in the same direction from both ends of the core body 21, and is a laminate (or a stack) of many rolled silicon steel sheets, each coated with a thin insulating layer. The magnetic core 20 used in this embodiment is obtained by laminating sheets that has been die-cut into a U shape as mentioned above or by winding a rolled silicon steel strip several times and dividing the resulting winding into two parts. In this embodiment, 0.35 mm-thick rolled silicon steel sheets are used.

It should be noted that the cross sectional shape of the sheet or strip perpendicular to the longitudinal direction of the legs 22 and 26 is a rectangle (a square or a rectangle), or a circle (not shown).

A set of conductive layers 12a-12n wound around the leg 22 in different levels or a set of conductive layers 12a'-12n' wound around the leg 22 in concentric layers is referred to as the conductor 12, and a set of conductive layers 16a-16n wound around the leg 26 in different levels or a set of conductive layers 16a-16n' wound around the leg 26 in concentric layers is referred to as the conductor 16.

The material of each of the conductive layers 12a-12n and 16a-16n stacked in different levels and the conductive layers 12a-12n' and 16a'-16n' arranged in concentric layers is a wire.

The wire is, for example, a long copper wire having a rectangular (square or rectangular) cross section, and an insulating coating is formed on its surface. An example of the wire has a thickness of 0.9 mm and a height of 1.6 mm. The insulating coating is made of a urethane resin and its thickness is reduced to allow heat dissipation from the surface of the conductors 12 and 16. In this embodiment, the thickness of the insulating coating is 20 μm. (It should be noted that the cross section of the wire is sometimes indicated in a circle for ease of illustration, but the cross section thereof is actually rectangular, as mentioned above.)

How to wind the wires around each of the legs 22 and 26 is described. A single wire is wound several times around and along the outer periphery of the leg 22 with its one side surface facing the outer periphery of the leg 22, and then, in the same manner, the rest of the wire is wound several times around and along the outer periphery of the leg 26 in the opposite direction. Since the surface of the wire is covered with an insulating coating and the conductors 12 and 16 themselves generate less heat as a whole, as described later, there is no need to provide cooling gaps 300, which are conventionally required, between the wires (see FIG. 10), and thus the wires can be wound in close contact with each other. Therefore, the size of the device can be reduced by the volume of the cooling gaps 300, which are conventionally required.

In this case, a single wire is wound for each level around the legs 22 and 26, as described above, but for ease of explanation, a set of wires wound around the leg 22 and a set of wires wound around the leg 26 are referred to as a conductor 12 and a conductor 16, respectively.

The wires may be wound in another way (not shown). Two wires are prepared, and one of the wires is wound several times around and along the outer periphery of the leg 22 with its one side surface facing the outer periphery of the leg 22, while the other wire is wound several times around and along the outer periphery of the leg 26 in the same manner. Then, the layer of each of the wires wound around the leg 22 and the layer of each of the wires wound around the leg 26 may be connected by a connecting line.

The casing 1 for housing the magnetic core 20 and the conductors 12 and 16 wound around the legs 22 and 26 of the magnetic core 20 is made of a resin (ABS here) and includes a casing body 2 with a top opening and a lid 5 that covers the opening. The lid 5 is fastened with bolts (not shown) to close the top opening.

The affected area contact surface 9 of the casing body 2, which is to be brought into contact with the affected area of the patient, has bulging protrusions 7.

The tip 28 of the leg 22 and the tip 28 of the leg 26 of the magnetic core 20 housed in the casing 1 fit into recesses formed on the underside of the protrusions 7 of the lid 5 that covers the casing body 2.

The tip 28 of the leg 22, on which the conductor 12 is wound in different levels or in concentric layers, and the tip 28 of the leg 26, on which the conductor 16 is wound in different levels or in concentric layers, protrude slightly (3 mm in the present embodiment) from the conductors 12 and 16, and these protruding portions fit into the recesses on the undersides of the protrusions 7, as described above. It should be noted that the tips 28 of the legs 22 and 26 are held in close contact with (or at a small distance from) the recesses on the undersides of the protrusions 7, and the magnetic core 20 is fastened to the casing body 2 by a fastening member (not shown) or by another method such as bonding.

For each of the structures (first and second embodiments), there are two methods for connecting the conductor 12 wound around the leg 22 in different levels or in concentric layers and the conductor 16 wound around the leg 26 in different levels or in concentric layers.

FIG. 3 shows a cross-sectional view of the magnetic stimulation device A of the present invention and partial enlarged views of the first and second structures (first and second embodiments) of the conductors 12 and 16. It should be noted that in the accompanying drawings, the conductors 12 and 16 are illustrated as if the adjacent wires or layers were wound at a distance from each other for ease of illustration, but they can be wound in contact with each other, without any gap therebetween.

First Embodiment

The conductors 12 and 16 according to the first embodiment will be described with reference to FIG. 4 and FIG. 5.

As shown in FIG. 4 and FIG. 5, in the structure of the conductors 12 and 16 according to the first embodiment, an operation of winding a single wire around the legs 22 and 26 of the magnetic core 20 is repeated to form layers stacked in different levels. More specifically, a single wire is wound around the legs 22 and 26 on each of planes located at different levels and perpendicular to the longitudinal direction of the legs 22 and 26. This means that these planes are located at different levels between the tips of the legs 22 and 26 and the core body 21.

Therefore, the pair of the conductive layer 12a wound around the leg 22 and the conductive layer 16a wound around the leg 26 to the pair of the conductive layers 12n and 16n are each formed of a single wire, and stacked in different levels to form the first to nth conductive layers 12a-12n and the first to nth conductive layers 16a-16n.

Here, the number of the layers is counted in the following manner. The layer located closest to the tip 28 of the leg 22 or 26 is referred to as the first layer 12*a* or 16*a*, the layer adjacent to the first layer toward the core body 21 is referred to as the second layer 12*b* or 16*b*, and the layer located closest to the core body 21 is referred to as the nth layer 12*n* or 16*n*.

Throughout the present invention, the wire is wound in such a manner that the direction N (S) of the magnetic field in the leg 22 is opposite to the direction S (N) of the magnetic field in the leg 26.

More specifically, in FIG. 4, when wires are wound counterclockwise to form the left conductive layers 12*a*-12*n*, the wires are wound clockwise to form the right conductive layers 16*a*-16*n*. Between the pair of legs 22 and 26, the end of the wire of each of the left conductive layers 12*a*-12*n* and the corresponding end of the wire of each of the right conductive layers 16*a*-16*n* are connected to form a single wire.

In addition, the wires of the conductive layers 12*a*-12*n* and 16*a*-16*n* wound around the legs 22 and 26 are connected in parallel at their one ends to form the conductors 12 and 16, respectively, and then connected to excitation current supply lines 10 and 14 connected to an external power source. In other words, the wires of the parallel-connected conductive layers 12*a*-12*n* and 16*a*-16*n* have a structure in which each of the portrait-oriented strip-shaped conductors 120 and 160 in the conventional example shown in FIG. 10 to be described later is divided into several wires.

FIG. 4 (and also FIG. 5 to be described later) shows an example where the wire of each layer is wound in a circular spiral shape, but as shown in FIG. 2 and FIG. 6 and FIG. 7 to be described later, the wire may be wound in a rectangular spiral shape in plan view to conform to the cross-sectional shape of the legs 22 and 26 of the magnetic core 20.

Between the pair of the legs 22 and 26, the wires of the conductive layers 12*a*-12*n* around the leg 22 are respectively connected, at each level, to the wires of the corresponding conductive layers 16*a*-16*n* around the leg 26.

Next, the case where the magnetic stimulation device A configured as described above according to the first embodiment is turned on.

When an excitation current (a pulse current or an alternating current) is supplied from one excitation current supply line 10, the excitation current is shunted. The current flows counterclockwise through the parallel conductive layers 12*a*-12*n* wound around the leg 22, flows clockwise through the parallel conductive layers 16*a*-16*n* wound around the leg 26, and then flows to the other excitation current supply line 14. As a result, the tip 28 of the leg 22 has a south magnetic pole S, while the tip 28 of the leg 26 has a north magnetic pole N.

When the flow of the excitation current in one direction ends, the flow is reversed. When the excitation current flows in the opposite direction from the excitation current supply line 14, it is shunted. The current flows clockwise through the parallel conductive layers 16*a*-16*n* wound around the leg 26, flows counterclockwise through the parallel conductive layers 12*a*-12*n* wound around the leg 22, and then flows to the excitation current supply line 10. As a result, the magnetic polarity is reversed, i.e., the tip 28 of the leg 26 has a south magnetic pole S, while the tip 28 of the leg 22 has a north magnetic pole N. This is repeated at regular intervals. A magnetic flux G is generated between the tips 28 of the magnetic core 20.

Next, the operation of the magnetic stimulation device A of the present invention when it is turned on will be described, but first, the operation of the conventional example will be described with reference to FIG. 10.

FIG. 10 shows a conventional device developed by the present inventors. In this device, a U-shaped core 200 having a pair of legs 220 and 260, like the magnetic core 20 of the present invention, is used, and conductors 120 and 160 are respectively wound around the legs 220 and 260.

These conductors 120 and 160 each have a long, rectangular cross section, and are wound around the legs 220 and 260 in such a manner that the long side of the rectangle extends vertically along the outer periphery of the legs 220 and 260. Since the conductors 120 and 160 are each a portrait-oriented strip, the long side of the rectangular cross section extends vertically from the vicinity of the tips of the legs 220 and 260 to the core body. The thickness of the strip is, for example, 0.8 mm and the height is 9 mm. Cooling gaps 300 are provided between the layers of the conductors 120 and 160.

When an excitation current is supplied to these conductors 120 and 160, the tip 280 of the leg 220 has a north (or south) magnetic pole N (or S), while the tip 280 of the leg 260 has the opposite south (or north) magnetic pole S (or N), as described above.

The mechanism had not yet been elucidated when the present inventors developed the conventional device, but in developing the conventional device, they have found that the inductance of the tip regions of the legs 220 and 260 of the U-shaped core 200 are lower than that of the other regions, and as a result, a strong excitation current flows locally in the upper edge regions of the portrait-oriented conductors 120 and 160 near the tip regions and thus achieved the present invention. In other words, the current density of the tip-side upper edge regions of the conductors 120 and 160, with the rectangular cross section being in portrait orientation, is higher than that of the other regions, and as a result, the temperature rises abnormally in the upper edge regions of the conductors 120 and 160.

In addition, the present inventors have found that a magnetic flux leaked from the legs 220) and 260 passes through the conductors 120 and 160 from the inner side to the outer side (or in the opposite direction) and induces eddy currents U1, which flow in the conductors 120 and 160 while generating Joule heat, and have achieved the present invention.

In the conventional device, the conductors 120 and 160 are disposed with the rectangular cross section being in portrait orientation. Therefore, large eddy currents U1 flow vertically across the height of the conductors 120 and 160. The inventors have found that these large eddy currents U1 are also the cause of a temperature rise in the conductors 120 and 160.

More specifically, the inventors have found as follows. The conductors 120 and 160 are each a single copper strip with a large width and disposed with the rectangular cross section being in portrait orientation. Therefore, due to the synergistic effect of the biased current density and generation of the large eddy currents U1, the upper edge regions of the conductors 120 and 160 have an abnormal temperature rise. Since the inventors have not confirmed these findings, the conventional device requires cooling gaps 300 and a cooling mechanism for supplying a cooling gas to the cooling gaps 300.

In contrast, in the present invention, parallel-connected conductive layers 12*a*-12*n* and 16*a*-16*n*, which are equivalent to a configuration obtained by dividing the conventional portrait-oriented conductors 120 and 160 into two or more wires, are stacked in different levels along the longitudinal direction of the legs 22 and 26, based on these findings, so as to significantly eliminate the biased current density in each of the layers (particularly in the first layers 12a and 16a) and reduce the magnitude of an eddy current U2 generated in each layer. As a result, the inventors have succeeded in suppressing heat generation significantly in the conductors 12 and 16.

The above achievements will be described in more detail. In the first embodiment, the conductive layers 12a-12n and 16a-16n can be connected in the following two methods.

In the first connection method, the conductive layers 12a-12n are respectively connected in this order to the conductive layers 16a-16n, as shown in FIG. 4. In the second connection method, the conductive layers 12a-12n are respectively connected in reverse order to the conductive layers 16a-16n. In the second connection method, the connection order is reversed from that in the first connection method.

In the first connection method, the first layer 12a located closest to the tip 28 of the leg 22, among the conductive layers 12a-12n wound around the leg 22, is connected to the first layer 16a located closest to the tip 28 of the leg 26, among the conductive layers 16a-16n wound around the leg 26, and the nth layer 12n wound around the leg 22 and located closest to the core body 21 is connected to the nth layer 16n wound around the leg 26 and located closest to the core body 21. In the same manner, the second to (n-1)th layers 12b-12(n-1) around the leg 22 are connected in this order to the second to (n-1)th layers 16b-16(n-1) around the leg 26.

In contrast, in the second connection method, the first layer 12a located closest to the tip 28 of the leg 22, among the conductive layers 12a-12n wound around the leg 22, is connected to the nth layer 16n located closest to the core body 21, among the conductive layers 16a-16n wound around the leg 26, and the nth layer 12n wound around the leg 22 and located closest to the core body 21 is connected to the first layer 16a wound around the leg 26 and located closest to the tip 28 of the leg 26. The second to (n-1)th layers 12b-12(n-1) around the leg 22 are connected in reverse order to the (n-1)th to second layers 16(n-1)-16b around the leg 26.

In both cases, when an excitation current is supplied to the conductors 12 and 16, the tip 28 of the leg 22 has a north (or south) magnetic pole N (or S), while the tip 28 of the leg 26 has the opposite south (or north) magnetic pole S (or N). This is repeated alternately and thus a magnetic flux G is generated between the poles.

In the first connection method, when a current is supplied, the inductance of the tip regions of the legs 22 and 26 are lower than that of the other regions, as described above. Therefore, the amount of excitation current flowing in the first layers 12a and 16a wound around the tip regions is slightly greater than that flowing in the other layers 12b-12n and 16b-16n. This means that the amount of excitation current flowing in the conductive layers decreases as they get closer to the core body 21. However, unlike the conventional example in which the conductors are each formed of a single portrait-oriented strip, the conductors 12 and 16 are each composed of a plurality of divided wires and therefore the bias of the current density is reduced.

Like the conventional example, a leakage magnetic flux W from the legs 22 and 26 of the magnetic core 20 passes through the conductive layers 12a-12n and 16a-16n. In this case, however, since the conductors are divided into the conductive layers 12a-12n and 16a-16n, eddy currents U2 generated by the leakage magnetic flux W are much smaller than that generated in the conventional example with a wide strip conductor. This means that a small eddy current U2 is generated within a smaller area of each conductive layer, even if it is generated by the leakage magnetic flux W.

As a result, due to the significantly reduced bias of the current density and the smaller eddy current U2 generated within a smaller area of each of the conductive layers 12a-12n and 16a-16n, heat generation in the conductors 12 and 16 is significantly suppressed, compared to that in the conventional example.

In FIG. 3, the eddy currents U2 are illustrated outside the wire of each layer for easy understanding, but actually, they are generated within the wire.

FIG. 8 schematically shows the temperature rise distribution in the conductive layers 12a-12n and 16a-16n in this case. There is no significant difference in the temperature of the conductive layers 12a-12n and 16a-16n but the layer located closer to the tip 28 of the leg 22 or 26 has a higher temperature.

Next, the second connection method in the first embodiment will be described (FIG. 5). When an excitation current is supplied to the conductors 12 and 16, its flow is slightly biased toward the first layers 12a and 16a due to the difference in inductance as described above. However, in the nth layers 16n and 12n connected to these first layers 12a and 16a, the excitation current is harder to flow than in the first layers 12a and 16a, and therefore the amount of excitation current flowing in the first layers 12a and 16a is reduced as the nth layers 12n and 16n serve as limiting factors. In other words, the amount of the excitation current flowing in the first layers 12a and 16a is equal to that flowing in the nth layers 12n and 16n.

This relationship also applies not only to the second layers 12b and 16b and the (n-1)th layers 12(n-1) and 16(n-1) but also to the other layers connected in reverse order, and thus an almost constant and suppressed excitation current flows throughout the conductors 12 and 16.

As a result, heat generation can be suppressed more than in the first connection method shown in FIG. 5. It should be noted that the mechanism of the heat generation caused by the leakage magnetic flux W is the same as that in the case of FIG. 5.

FIG. 9 schematically shows the temperature rise distribution in the conductive layers 12a-12n and 16a-16n in this case. The temperatures of the conductive layers 12a-12n and 16a-16n are leveled off, compared to the case of FIG. 8.

Next, the second embodiment will be described. Unlike the first embodiment, the conductors 12 and 16 of the second embodiment are each composed of a plurality of wires that are closely wound around the leg 22 or 26 in the form of concentric coil springs of different diameters or dimensions from small to large. More specifically, the concentric layers of the conductors 12 and 16 are arranged in a nesting manner, with layers of smaller diameters or dimensions being nested within layers of larger diameters or dimensions. In the conductors 12 and 16, the innermost layers are referred to as the first layers 12a' and 16a', the layers adjacent to the first layers are referred to the second layers 12b' and 16b', and the outermost layers are referred to as the nth layers 12n' and 16n'.

Since the conductors 12 and 16 composed of the first to nth layers 12a'-12n' and 16a'-16n', respectively, can suppress the temperature rise in the conductors 12 and 16 in the same manner as in the first embodiment, they can be closely wound without any gap between the upper and lower wires and between the inner and outer layers.

As in the case of the first embodiment, between the legs 22 and 26, the wires of the conductive layers 12a'-12n' around the leg 22 are respectively connected to the wires of the conductive layers 16a'-16n' around the leg 26. The wire winding direction and connection between the legs 22 and 26 are determined so that the direction of the magnetic field in the leg 22 is opposite to that in the leg 26.

More specifically, if the conductive layers 12a'-12n' are wound clockwise around the leg 22, the conductive layers 16a'-16n' are wound counterclockwise around the leg 26, and the wires of the concentric conductive layers 12a'-12n' wound clockwise around the leg 22 are respectively connected, at each concentric position, to the wires of the corresponding conductive layers 16a'-16n' wound counterclockwise around the leg 26.

Furthermore, the wires of the conductive layers 12a-12n' wound around the leg 22 are connected in parallel to the leg 22, and the wires of the conductive layers 16a'-16n' wound around the leg 26 are connected in parallel to the leg 26.

When a current is supplied to the conductors 12 and 16, the excitation current flows downwardly (or upwardly) through the concentric conductive layers 12a'-12n' around the leg 22 and the concentric conductive layers 16a'-16n' around the leg 26. In this case, even if the inductance of the tip regions of the legs 22 and 26 is lower than that in the other regions 18, other than the tip regions of the legs 22 and 26, have higher inductance and serve as limiting factors. Thus, the amount of the excitation current flowing through the conductors 12 and 16 is adapted to the amount of excitation current flowing through the regions 18 other than the tip regions of the legs 22 and 26. In other words, the bias of the current density is significantly reduced.

Therefore, in this case, the temperature of the conductors 12 and 16 is kept relatively low and constant throughout the conductors 12 and 16, as shown in FIG. 9.

FIG. 3 schematically shows the regions 17 corresponding to the tip regions of the legs 22 and 26 and the regions 18 corresponding to the regions other than the tip regions of the legs 22 and 26.

There are also two connection methods in the second embodiment. The connection methods are basically the same as those in the first embodiment. These connection methods will be described below.

The first connection method is as shown in FIG. 6. Between the legs 22 and 26, the wires of the layers in the same concentric position are connected. Specifically, the innermost first layer 12a' is connected to the first layer 16a', and the second to nth layers around the leg 22 are connected to the second to nth layers around the leg 26 in this order from inside to outside.

The second connection method is as shown in FIG. 7. The innermost first layer 12a' located closest to the leg 22, among the conductive layers 12a'-12n' wound around the leg 22 in concentric layers, is connected to the outermost nth layer 16n' located farthest from the leg 26, among the conductive layers 16a'-16n' wound around the leg 26 in concentric layers. The outermost layer 12n' around the leg 22 is connected to the innermost first layer 16a' around the leg 26, among the layers wound around the leg 26 in concentric layers. The second to (n–1)th layers 12b'-12(n–1)' around the leg 22 are connected, in reverse order, to the (n–1)th to second layers 16(n–1)'-16b' around the leg 26.

As shown above, when a current is supplied, the inductance of the tip regions of the legs 22 and 26 are lower than the other regions, as described above. The effect of this phenomenon also becomes more pronounced in the tip-side inner layers in the radial direction. In other words, when the tip regions of the first layers 12a' and 16a' are compared with the tip regions of the outermost layers 12n' and 16n', the first layers 12a' and 16a' are more affected by this phenomenon.

As a result, the intensity of the excitation current flowing in the first layers 12a' and 16a' is slightly higher than that flowing in the outermost layers 12n' and 16n'.

In the first connection method, the layers 12a-12n' are connected to the layers 16a'-16n' in the same concentric position. For example, the first layer 12a' is connected to the first layer 16a' and the nth layer 12n' is connected to the nth layer 16n'. Therefore, the innermost first layers 12a' and 16a' are affected to some extent by the above-described phenomenon of inductance, while the outermost layers 12n' and 16n' are less affected than the first layers 12a and 16a'.

However, in this case, all the layers are wound around the legs 22 and 26 in a direction from the tip toward the core body 21, and therefore, the regions 18, other than the tip regions of the legs 22 and 26, serve as limiting factors and significantly cancel the above effect.

As a result, in the second embodiment, even if the first connection method is adopted, the bias of the current density is much smaller than that in the first connection method in the first embodiment and thus the temperature rise can be suppressed more effectively.

In the second connection method, the layers 12a'-12n' around the leg 22 are connected to the layers 16a'-16n' around the leg 26 in reverse order. For example, the first layer 12a' (or 16a') is connected to the nth layer 16n' (or 12n'). Therefore, in a combination of the first layer 12a' and the nth layer 16n' connected in reverse order, the regions 18 of the nth layers 16n' and 12n' which are least affected by the phenomenon of inductance, other than the tip regions of the legs 22 and 26, serve as limiting factors. This relationship also applies to the other combinations of layers. In the second connection method in the second embodiment, the bias of the current density is smaller than that in the first connection method and thus the temperature rise can be suppressed more effectively.

As described above, the temperature rise in the conductors 12 and 16 in the second embodiment is as shown in FIG. 9, although the actual temperature may be slightly different.

Experimental Examples

FIG. 11 is a graph showing a comparison of the time course of the temperature rise in the conventional example shown in FIG. 10 as a comparative example, the first connection method in the first embodiment, and the second connection method in the first embodiment.

In this figure, solid lines indicate the second connection method in the first embodiment, broken lines indicate the first connection method in the first embodiment, and dot-dash lines indicate the conventional example.

The thin lines each indicate the temperature of a conductive layer located in the center of the core leg, and the thick lines each indicate the temperature of a conductive layer located in the tip region of the core leg. The unit is ° C. As a power source, a pulse power source with a capacitance of 120 μF was used. The output voltage was fixed at 420 V and compared. The experiment conditions were as follows.

Comparative Example

Cross section of conductive wire: 0.8 mm×9 mm, Single wire
Output voltage of power source: 420 V
Magnetic flux density (Center between cores): 0.64 T
Excitation current: 1100 A

First Embodiment

Cross section of conductive wire: 0.9 mm×1.6 mm, Five wires
Output voltage of power source: 420 V
Magnetic flux density (Center between cores): 0.62 T
Excitation current: 1100 A In the comparative example, the temperature of the conductive layer located in the tip region of the leg reached 80° C. in 70 seconds after a current was supplied. However, it took 130 seconds in the first connection method in the first embodiment and 190 seconds in the second connection method in the first embodiment.

Thereby, with the use of the device of the present invention, the successive magnetic treatment time could be extended significantly.

This principle suggests that the successive magnetic treatment time can be extended significantly also in the second embodiment.

REFERENCE SIGNS LIST

A: Magnetic stimulation device
G: Magnetic flux
U1, U2: Eddy currents
W: Leakage magnetic flux
1: Casing
2: Casing body
5: Lid
7: Protrusion
9: Affected area contact surface
10, 14: Excitation current supply lines
12, 16: Conductors
12a-12n, 16a-16n/12a'-12n', 16a'-16n': Conductive layers (first layer to nth layer)
17: Region corresponding to a core tip region
18: Region corresponding to a region other than the core tip region
20: Magnetic core
21: Core body
22, 26: Legs
28: Tip of a leg
120, 160: Conductors
200: U-shaped core
220, 260: Legs
280: Tip
300: Cooling gap

The invention claimed is:

1. A magnetic stimulation device comprising:
a magnetic core including: a core body; and a pair of legs including a first leg and a second leg each extending from the core body; and
conductors including: a conductor having conductive layers that are wound around the first leg and stacked in different levels; and a conductor having conductive layers that are wound around the second leg and stacked in different levels, wherein
an ordinate number of the conductive layers is counted in such a manner that a layer located closest to a front end of the first or second leg is referred to as a first layer, a layer adjacent to the first layer toward the core body is referred to as a second layer, and a layer closest to the core body is referred to as an nth layer,
the conductive layers are each formed of a wire having a rectangular cross section that is parallel to a longitudinal direction of the first leg and the second leg,
between the first leg and the second leg, the wires of the conductive layers around the first leg are connected to the wires of the conductive layers around the second leg,
the first layer wound around the first leg is connected to the nth layer wound around the second leg,
the nth layer wound around the first leg is connected to the first layer wound around the second leg,
the second to (n−1)th layers wound around the first leg are respectively connected in reverse order to the (n−1)th to second layers around the second leg, and
remaining ends of the wires of the conductive layers wound around each of the first and second legs are connected in parallel for the individual first and second legs, respectively.

2. A magnetic stimulation device comprising:
a magnetic core having a U-shape and including: a core body; and a pair of legs including a first leg and a second leg each extending in the same direction from the core body; and
conductors including: a conductor having conductive layers that are wound around the first leg in concentric layers of different diameters or dimensions; and a conductor having conductive layers that are wound around the second leg in concentric layers of different diameters or dimensions, wherein
an ordinate number of the conductive layers is counted in such a manner that a layer located closest to the first or second leg is referred to as a first layer, a layer adjacent to the first layer in a direction away from the first or second leg is referred to as a second layer, and a layer farthest from the first or second leg is referred to as an nth layer,
the conductors are each formed of wires having a rectangular cross section that is parallel to a longitudinal direction of the first leg and the second leg,
between the first leg and the second leg, the wires of the conductive layers around the first leg are connected to the wires of the conductive layers around the second leg,
the first layer wound around the first leg is connected to the nth layer wound around the second leg,
the nth layer wound around the first leg is connected to the first layer wound around the second leg,
the second to (n−1)th layers wound around the first leg are respectively connected in reverse order to the (n−1)th to second layers wound around the second leg, and
remaining ends of the wires of the conductive layers wound around each of the first and second legs are connected in parallel for the individual first and second legs, respectively.

* * * * *